(12) United States Patent
Zellner et al.

(10) Patent No.: US 8,510,394 B2
(45) Date of Patent: Aug. 13, 2013

(54) METHOD OF FACILITATING ACCESS TO IP-BASED EMERGENCY SERVICES

(75) Inventors: Samuel N. Zellner, Dunwoody, GA (US); Mark J. Enzmann, Roswell, GA (US); Robert T. Moton, Jr., Alpharetta, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 113 days.

(21) Appl. No.: 12/768,166

(22) Filed: Apr. 27, 2010

(65) Prior Publication Data

US 2010/0205534 A1  Aug. 12, 2010

Related U.S. Application Data

(60) Division of application No. 11/591,058, filed on Nov. 1, 2006, now Pat. No. 7,730,125, and a continuation of application No. 10/738,894, filed on Dec. 16, 2003, now Pat. No. 7,149,774, and a continuation of application No. 09/586,065, filed on Jun. 2, 2000, now abandoned.

(51) Int. Cl.
*G06F 15/16* (2006.01)

(52) U.S. Cl.
USPC ........... 709/206; 709/200; 709/204; 709/224; 716/733; 704/270; 704/271; 370/39; 370/37; 370/38; 370/42; 370/45

(58) Field of Classification Search
USPC ................. 715/733; 709/206, 224, 200, 204; 704/270, 271; 370/33, 37, 38, 42, 45
See application file for complete search history.

(56) References Cited

U.S. PATENT DOCUMENTS

| | | | |
|---|---|---|---|
| 4,760,593 A | | 7/1988 | Bissonnette et al. |
| 5,333,171 A | | 7/1994 | Wang et al. |
| 5,438,568 A | | 8/1995 | Weisser, Jr. |
| 5,558,638 A | * | 9/1996 | Evers et al. ..................... 604/66 |
| 5,559,864 A | * | 9/1996 | Kennedy, Jr. ............... 455/412.1 |
| 5,568,535 A | * | 10/1996 | Sheffer et al. ................... 379/39 |
| 5,576,952 A | * | 11/1996 | Stutman et al. ............... 600/300 |
| 5,589,818 A | | 12/1996 | Queen |
| 5,654,690 A | * | 8/1997 | Ishikawa et al. .............. 340/506 |
| 5,717,379 A | | 2/1998 | Peters |
| 5,812,054 A | | 9/1998 | Cohen |
| 5,884,032 A | | 3/1999 | Bateman et al. |
| 5,912,963 A | * | 6/1999 | Begeja et al. ............ 379/221.01 |
| 5,978,855 A | * | 11/1999 | Metz et al. ..................... 709/249 |
| 5,991,806 A | * | 11/1999 | McHann, Jr. ................. 709/224 |
| 6,028,514 A | * | 2/2000 | Lemelson et al. ........ 340/539.13 |
| 6,052,052 A | * | 4/2000 | Delmonaco .............. 340/539.11 |

(Continued)

OTHER PUBLICATIONS

An online article, "Samsung Integrate Digital Camera and Phone," published on Jul. 1, 2000, and retrieved from http://www.dpreview.com/news/0007/00070101 samsungdigiphone,asp on Aug. 10, 2000 (2 pgs.).

(Continued)

*Primary Examiner* — Anthony Mejia
(74) *Attorney, Agent, or Firm* — Cantor Colburn LLP

(57) ABSTRACT

A method of responding to an emergency includes monitoring for an internet protocol based help request message; receiving the help request message; evaluating the help request message and additional information; and dispatching emergency help in response to the help request message and the additional information.

13 Claims, 5 Drawing Sheets

(56) References Cited

U.S. PATENT DOCUMENTS

| | | | |
|---|---|---|---|
| 6,094,134 A | 7/2000 | Cohen | |
| 6,131,067 A | 10/2000 | Girerd et al. | |
| 6,154,690 A * | 11/2000 | Coleman | 701/1 |
| 6,198,394 B1 * | 3/2001 | Jacobsen et al. | 340/573.1 |
| 6,199,045 B1 | 3/2001 | Giniger et al. | |
| 6,271,751 B1 | 8/2001 | Hunt et al. | |
| 6,288,642 B1 * | 9/2001 | Dohrmann | 340/540 |
| 6,292,542 B1 * | 9/2001 | Bilder | 379/45 |
| 6,294,993 B1 * | 9/2001 | Calaman | 340/539.18 |
| 6,295,346 B1 | 9/2001 | Markowitz et al. | |
| 6,302,844 B1 | 10/2001 | Walker et al. | |
| 6,324,183 B1 * | 11/2001 | Miller et al. | 370/467 |
| 6,330,449 B1 | 12/2001 | Kim | |
| 6,330,499 B1 | 12/2001 | Chou et al. | |
| 6,356,841 B1 | 3/2002 | Hamrick et al. | |
| 6,415,018 B1 * | 7/2002 | Antonucci et al. | 379/45 |
| 6,442,241 B1 | 8/2002 | Tsumpes | |
| 6,487,684 B1 * | 11/2002 | Ishii | 714/44 |
| 6,504,909 B1 | 1/2003 | Cook et al. | |
| 6,510,344 B1 * | 1/2003 | Halpern | 607/32 |
| 6,519,241 B1 | 2/2003 | Theimer | |
| 6,553,106 B1 | 4/2003 | Gould et al. | |
| 6,563,910 B2 * | 5/2003 | Menard et al. | 379/45 |
| 6,567,502 B2 | 5/2003 | Zellner et al. | |
| 6,570,503 B1 * | 5/2003 | Ulert et al. | 340/573.1 |
| 6,577,234 B1 * | 6/2003 | Dohrmann | 340/540 |
| 6,618,714 B1 * | 9/2003 | Abrahams | 706/45 |
| 6,728,341 B1 * | 4/2004 | Puchek et al. | 379/49 |
| 6,741,165 B1 * | 5/2004 | Langfahl et al. | 340/426.1 |
| 6,766,007 B1 * | 7/2004 | Dermler et al. | 379/201.01 |
| 6,807,564 B1 | 10/2004 | Zellner et al. | |
| 7,163,144 B1 * | 1/2007 | Trelawney et al. | 235/379 |
| 7,238,156 B1 | 7/2007 | Adamczyk | |
| 7,406,710 B1 * | 7/2008 | Zellner et al. | 726/14 |
| 7,525,567 B2 * | 4/2009 | McCutchen | 348/46 |
| 7,991,380 B2 * | 8/2011 | Collins et al. | 455/404.1 |
| 8,108,218 B1 * | 1/2012 | Huboi | 704/275 |

OTHER PUBLICATIONS

Daniel L. Lough et al., "A Short Tutorial on Wireless LANS and IEEE 802.11," retrieved from http://computer.org/students/looking/summer97/ieee802.htm on Sep. 7, 2000 (5 pgs.).

Description of ITI Wireless Intrusion Sensors, pp. 1-3, available on Feb. 22, 2000 at http://www.flex.com/-digital/itwis.html.

* cited by examiner

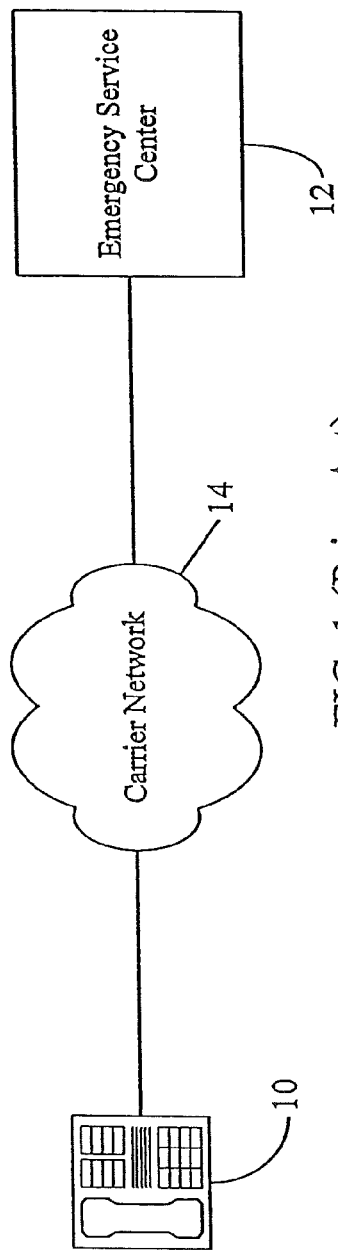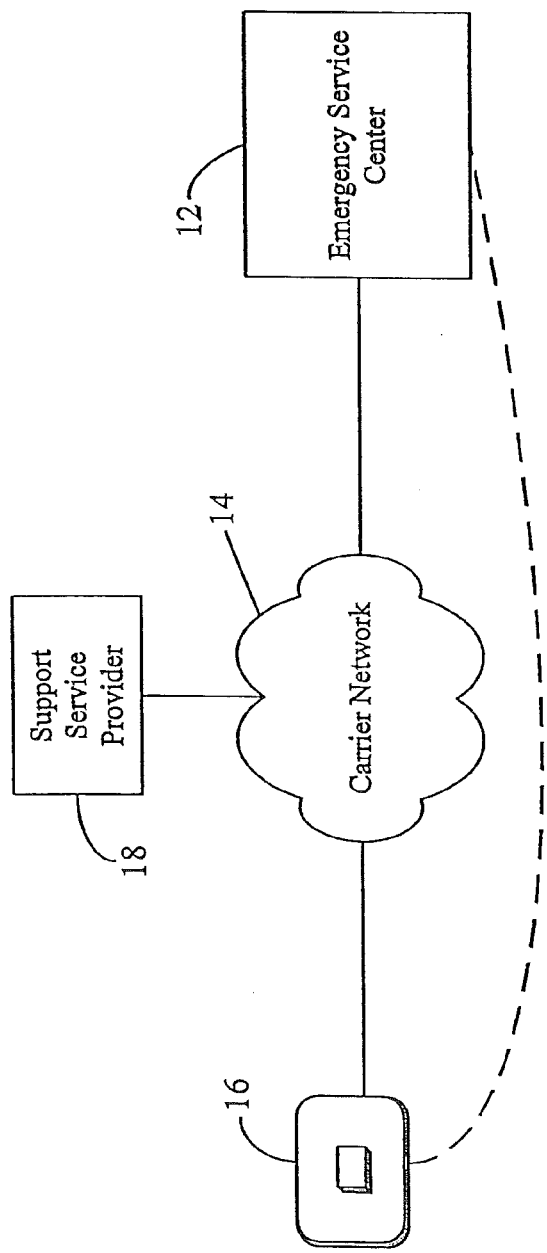

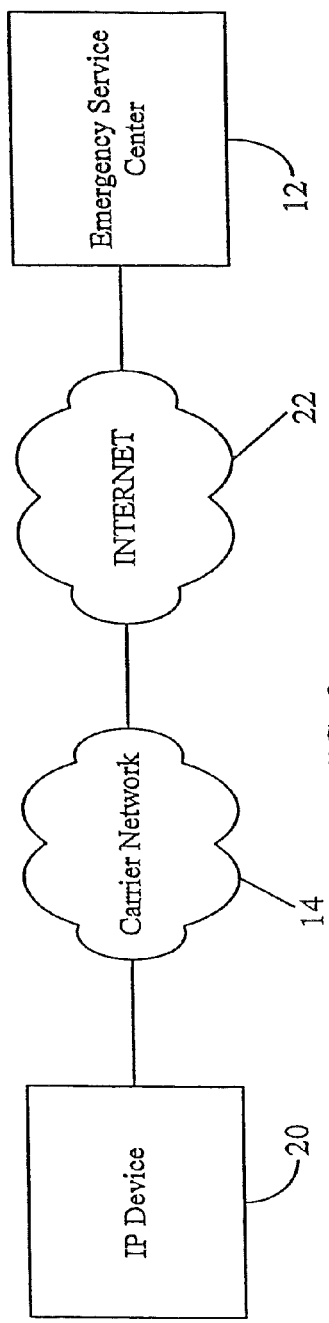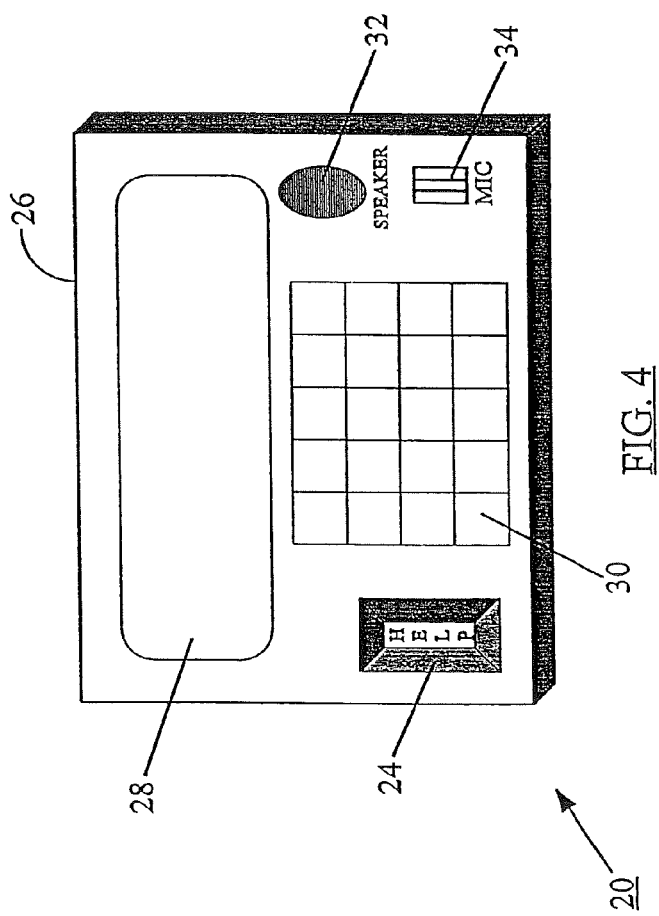

METHOD OF FACILITATING ACCESS TO IP-BASED EMERGENCY SERVICES

CROSS-REFERENCE TO RELATED APPLICATIONS

This application is a divisional of U.S. patent application Ser. No. 11/591,058 filed Nov. 1, 2006, the contents of which are incorporated by reference herein in their entirety, which is a continuation of U.S. patent application Ser. No. 10/738,894 filed Dec. 16, 2003, now U.S. Pat. No. 7,149,774, the contents of which are incorporated by reference herein in their entirety, which is a continuation of U.S. patent application Ser. No. 09/586,065 filed Jun. 2, 2000, now abandoned, the contents of which are incorporated by reference herein in their entirety.

BACKGROUND OF THE INVENTION

1. Field of the Invention

The present invention broadly relates to emergency reporting services, and more particularly, to an emergency reporting service that employs TCP/IP (Transmission Control Protocol/Internet Protocol) messaging to report a user's emergency condition to an emergency service center (e.g., the police).

2. Description of the Related Art

FIG. 1 illustrates a typical prior art emergency reporting arrangement using a telephone 10. A person in need of emergency help dials a designated emergency reporting number (e.g., '911') to connect to an emergency service center (ESC) 12. The emergency service center 12 may be a 911 response center, a police station, a hospital, a fire station, a combination of these places or any other location equipped for dispatching emergency relief. A carrier network 14 may electrically connect the telephone 10 to a receiving apparatus (e.g., an operator headset receiver) at the ESC 12. The carrier network 14 may include, individually or in combination, the plain old telephone system (POTS), the more advanced public switched telephone network (PSTN), or a wireless communication network (e.g., a cellular phone network) when the telephone 10 is, for example, a cellular phone ("cell phone").

Instead of dialing all the digits contained in the designated emergency reporting number (e.g., '9', '1', '1'), a user may instead "speed dial" the number by programming a single key on the telephone 10. In this manner, the user need not press individual digits of the phone number, but, instead, may need to press only a pre-marked speed dial key. Some modern cell phones come equipped with a "button" or key on their keypads that is dedicated to dial a predetermined emergency phone number (e.g., '911').

Another emergency reporting device is shown in FIG. 2, which depicts a prior art "panic button" 16 in communication with the emergency service center 12. The panic button 16 may be broadly categorized as a wearable wireless transmitter that finds applications in situations when the user may not easily access the telephone 10 or when the user is not able to dial the ESC's 12 telephone number. Users of the panic button 16 may include, among others, elderly people and people with delicate health. Normally the user wears the panic button 16 around the user's neck and presses the panic button when an emergency condition arises. The panic button 16 wirelessly transmits an "alarm signal" to a base unit or receiving device (not shown) attached to the user's phone line. The alarm signal instructs the base unit to initiate a phone call to a preprogrammed phone number, usually the phone number of an establishment or company that provides support services and maintenance for such panic buttons in a given geographical area.

A support service provider (SSP) 18 receives the phone call from the base unit of the panic button 16 via the carrier network 14. The base unit may send over the phone line an identification code or number pre-assigned to the panic button 16 by the SSP 18. Therefore, an operator at the SSP 18 may immediately compare the received identification code with a customer database to identify the user of the panic button 16. Upon identifying the user, the operator in the SSP's 18 facility may place a phone call to the ESC 12 giving requisite information (e.g., the name of the person in distress, the location where help is needed, any known medical history of the person requiring emergency help, etc.) to the operator or relief help dispatcher at the ESC 12. All such information may be stored in the SSP's 18 customer database (not shown) when the panic button 16 is assigned to a particular user. Instead of manual database look-up, the SSP 18 may implement an automatic database search and comparison process to instantly identify the operator of the panic button 16 as soon as an alarm indication is received from the base unit.

Normally, the carrier network 14 in the panic button application of FIG. 2 is a wireline network, e.g., the POTS or the PSTN. However, in a situation involving close monitoring of the elderly or the disabled (e.g., monitoring of patients in a large hospital complex), the panic button technology may be employed via a local wireless carrier network 14. The patient may activate the personal panic button 16 and the carrier network 14 may wirelessly transfer the help request to appropriate staff or emergency relief personnel in the hospital's ESC 12. The SSP 18 may not be needed in such an environment as symbolically indicated by the direct dotted connection between the panic button 16 and the ESC 12.

From the foregoing, it can be observed that the prior art devices used to report emergency conditions (e.g., the telephone 10 in FIG. 1 and the panic button 16 in FIG. 2) primarily send emergency help request messages through telephone signals in a circuit-switched telephone environment, i.e., in a telephone environment that "dedicates" an actual physical circuit between the caller and the called party. This "traditional" approach to request emergency help by calling '911' may not be effective sometimes, for example, when the person in need of help cannot dial the numbers to place a '911' call or when that person cannot orally respond to the questions of an operator receiving the '911' call. Furthermore, the operators or assistants receiving phone calls at the ESC 12 may get swamped by a large number of phone calls and may need to put the last caller on hold prior to reviewing the caller's emergency situation. This may not be desirable, especially when the caller's situation demands prompt and instant attention. Additionally, the ESC 12 or the SSP 18 may have a finite number of incoming telephone lines. In that situation, because of the circuit-switched nature of telephone communications, the person placing the emergency call may end up receiving a line "busy" signal instead of an operator's voice.

The availability of modern high-speed data processors and the continually growing popularity of the Internet make it desirable to offer an emergency reporting device that is capable of reporting a user's need for emergency help using TCP/IP message packets sent over the Internet to the ESC 12. It is also desirable for the support service provider 18 or a telephone company (telco) to offer a subscription-based or usage-based emergency reporting service using TCP/IP messaging over the Internet.

SUMMARY OF THE INVENTION

One embodiment includes a method of responding to an emergency includes monitoring for an internet protocol based help request message; receiving the help request message; evaluating the help request message and additional information; and dispatching emergency help in response to the help request message and the additional information.

An alternate embodiment includes a device for requesting emergency assistance, comprising: a processing unit; an emergency alert activation function coupled to the processing unit, wherein the emergency alert activation function is configured to send a first indication to the processing unit, wherein the sending of the first indication is in response to a user of the device activating the emergency alert activation function; a communication module coupled to the processing unit, wherein the processing unit is configured to send a second indication to the communication module, wherein the sending of the second indication is in response to the first indication, and wherein the communication module is configured to deliver a help request message in to an emergency service center (ESC), wherein the delivering of the help request message is in response to the second indication.

BRIEF DESCRIPTION OF THE DRAWINGS

Further advantages of the present invention may be better understood by referring to the following description taken in conjunction with the accompanying drawings, in which:

FIG. 1 illustrates a typical prior art emergency reporting arrangement using a telephone;

FIG. 2 depicts a prior art "panic button" in communication with an emergency service center;

FIG. 3 shows a schematic of a setup whereby an IP device according to the present invention sends emergency help request messages to an emergency service center over the Internet;

FIG. 4 is an illustration of an embodiment of the IP device of the present invention wherein the IP device has a physically built-in panic button;

DETAILED DESCRIPTION OF PREFERRED EMBODIMENTS

Figure 5:
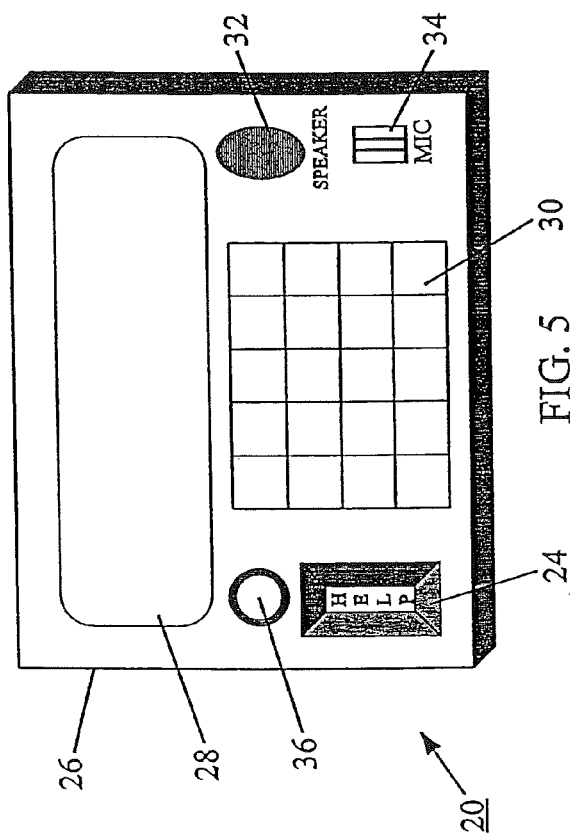
FIG. 5 illustrates another embodiment of the IP device having a built-in digital camera.

FIG. 3 shows a schematic of a setup whereby an IP (Internet Protocol) device 20 according to the present invention sends emergency help request messages to the emergency service center (ESC) 12 over the Internet 22 or any similar IP-based network. The IP device 20 (described hereinbelow in more detail) sends the emergency help request via a TCP/IP (Transmission Control Protocol/Internet Protocol) message sent over the Internet 22 to the ESC 12. The carrier network 14 is shown connecting the IP device 20 to the Internet 22. However, it is known that the physical infrastructure (e.g., telephone or cable lines, switches, etc.) of the carrier network 14 may form part of the Internet 22. For example, the carrier network may be a wireline telephone network, e.g., the POTS or the PSTN, or may be a combination of a wireline and wireless telephone network (e.g., a cellular telephone network). Therefore, the TCP/IP messages sent by the IP device 20 may share the same physical network infrastructure with voice communication traffic.

It is noted at the outset that, for the sake of convenience and ease of description, the same numerals are used to identify same or similar functionality throughout the figures. For example, both the emergency service center in FIG. 1 and that in FIG. 3 are identified by numeral '12'. As in FIG. 1, the ESC 12 in FIG. 3 may represent a police station, a fire station, a hospital, etc. However, the ESC 12 in FIG. 3 may further be equipped to receive and/or transmit TCP/IP messages over the Internet 22. Thus, in some situations, the ESC in FIG. 1 and that in FIG. 3 may not have identical operational hardware and software, but both of them may perform the same function, i.e., to dispatch emergency relief in response to an emergency help request.

The IP device 20 may be connected to the carrier network 14 via a regular telephone line. In one embodiment, a base unit (not shown) for the IP device 20 may be connected to the telephone line and the IP device 20 may be carried on the user's person. Any TCP/IP messages generated by the IP device 20 may be wirelessly transmitted first to the base unit, which, in turn, may forward them to the carrier network 14 using the telephone line. The TCP/IP messages may then be routed to the ESC 12 via the Internet 22. In another embodiment, the IP device 20 may utilize a wireless telephone network (e.g., the TDMA (Time Division Multiple Access) cellular network) as the carrier network 14 to initially transmit TCP/IP message packets to. Thereafter, the wireless network, in combination with the PSTN and the Internet 22, may route the TCP/IP packets to the ESC 12. In such an event, the carrier network 14 may be construed to include the PSTN and the wireless network.

The term "IP device" may be construed to include a number of devices equipped with panic button and capable of TCP/IP-based data communication when the panic button is activated. The panic button functionality may be accomplished with a hardware panic button (for example, the panic button 24 in FIG. 4) or a software panic button (described hereinbelow with reference to FIG. 7). The IP devices may include commercially available gadgets such as a wireless pager, a cellular telephone, a hand-held computing device (similar, e.g., to a PalmPilot), etc., modified to include the panic button functionality as described hereinbelow. Alternatively, a number of household devices, e.g., an alarm clock or a refrigerator, may be equipped with Internet access capability and a panic button to be covered by the term "IP device."

The carrier network 14 may be a wireline communication network, e.g., the POTS or the PSTN, or an ISDN (Integrated Services Digital Network), or a wired LAN (local area network). Alternatively, the carrier network 14 may be a wireless communication network, e.g., an AMPS (Advanced Mobile Phone Service) analog or digital wireless network, a wireless LAN, a WLL (Wireless Local Loop) or a TDMA (Time Division Multiple Access) cellular telephone network. The IP device 20 may take a number of different forms depending, for example, on the carrier network the IP device 20 is being used with. For example, in the configuration of FIG. 9, the carrier network 14 may be a WLL and the IP device 20 may be a wireless handset, or even a cellular phone handset, that transmits TCP/IP messages over RF (Radio Frequency) channels to the WLL central switching facility via a local base station. The central switching facility may be managed by the support service provider (SSP) 18. The SSP 18 may then transmit the received emergency help request messages to the ESC 12 over the Internet 22.

The IP device 20 may communicate with the ESC 12 using, for example, the instant messaging functionality supported by an IP-based network, e.g., the Internet 22. The instant messaging feature allows the IP device 20 to establish a direct session or a virtual connection with the remote ESC 12 via the Internet 22. In one embodiment, the IP-based network (here, the Internet 22), and preferably the carrier network 14 as well, may employ "classes of service" or "quality of service" classification schemes for data packets handled by the network. Some parameters that affect a network's classification scheme include, for example, the data bandwidth required, the latency to be tolerated during a message transmission and the acceptable error-rate during a message transmission. For example, in the case of routine e-mail or "chat" messages, more latency may be tolerated. However, the IP-based network may establish that certain emergency messages (e.g., messages originating from the IP device 20) or other messages (e.g., video conferencing data) requiring instant transmission of the message without delay may be assigned the highest priority or "class of service" when the IP network has to allocate its data transmission bandwidth among the competing data packets.

FIG. 4 is an illustration of an embodiment of the IP device 20 of the present invention wherein the IP device 20 has a physically built-in panic button 24. The. IP device 20 may be a portable or wearable unit. Alternatively, the IP device 20 may be a normally non-moving or fixed unit such as, for example, a household appliance (e.g., a refrigerator or an alarm clock) that is equipped with, for example, a web browser to access the Internet as described hereinbelow. When the IP device 20 is portable, it may have an associated base unit (not shown) to transmit appropriate signals to the carrier network 14. For example, the IP device 20 may communicate wirelessly with its corresponding base unit and the base unit may be physically connected to a telephone line to forward messages received from the IP unit 20 to the carrier network 14, which, here, may be the PSTN. The panic button 24 is shown installed in a housing 26, which additionally includes a display screen (or "display") 28, a keypad or keyboard 30, a speaker 32 and a microphone 34. In the case of a hand-held, portable IP device 20, the housing 26 may be built of relatively hard and unbreakable plastic or a shock-resistant ABS (Acrylonitrile Butadiene Styrene) material so that to allow a user, for example, to carry around the IP device 20 on his/her person. The electronic circuit blocks within the housing 26 are described hereinbelow with reference to FIG. 6. The housing 26 may include a source of electrical power (e.g., a storage battery) to provide requisite power to various circuit elements therein.

The panic button or the help button 24 may be provided on the housing 26 in a number of different ways. For example, in one embodiment, the panic button 24 may be a push-button or a key similar to a key on a computer keyboard. However, in another embodiment, the panic button 24 may be a membrane key. Similarly, the keys or "buttons" on the keypad 30 may be provided as, for example, push-button keys or computer keyboard-type keys or membrane keys or any other suitable design configuration. The choice of the type of panic button 24 and the type of keys on the keypad 30 may thus depend on design and aesthetic considerations including, for example, the size, the weight and the desired physical contours for the IP device 20. The user of the IP device 20 may need to push the panic button 24 only once to transmit the emergency request message in the TCP/IP form.

The display screen 28 may display text or graphic messages thereon. For example, when the IP device 20 functions as a pager, the display screen 28 may function as a routine display available on a paging device to display the messages received by the IP device 20. In one embodiment, the display screen 28 may be an LCD (liquid crystal display) display. In alternative embodiments, the display screen may be a TFT (thin film transistor) active matrix display or a touch-sensitive screen. A touch-sensitive display screen may be useful when the panic button functionality is implemented in software as discussed hereinbelow with reference to FIG. 7. In that case, the user of the IP device 20 may simply touch an emergency help or panic button icon provided on the display screen 28 to activate the software panic button to transmit the emergency help request message.

As depicted in FIG. 4, the housing 26 may include built therein a speaker 32 and a microphone 34. In one embodiment, after invoking the emergency help functionality by pressing the panic button 24, the user of the IP device 20 may additionally speak into the microphone 34. The IP device 20 may be configured to transmit the user's voice over the Internet and to the ESC 12 by using known voice-over-IP methods. The user may also be able to listen to voice responses from the operator at the ESC 12 via the speaker 32. These voice responses may be transmitted over the Internet. Alternatively, if the IP device 20 is physically connected to a telephone line (e.g., a PSTN line), the ESC 12 may take control of that telephone line (if already busy) or may place a telephone call to the IP device 20 over that telephone line once the ESC 12 receives the emergency help request message from the IP device 20 over the Internet. The user of the IP device 20 may then be able to orally communicate with an operator at the ESC 12 via the speaker 32 and the microphone 34.

FIG. 5 illustrates another embodiment of the IP device 20 having a built-in digital camera or other image capture device 36. A miniature digital camera 36 may be built into the housing 26 to take quick snapshots, or motion pictures, of the environment surrounding the user of the IP device 20. The camera 36 may be activated when the panic button 24 is pressed by the user and the camera 36 may remain activated for a predetermined time thereafter (e.g., for 30-60 seconds) prior to automatically shutting off itself. The camera lens may rotate within the housing 26 to "cover" a circular view angle of (or approximately) 360.degree. The video information provided by images shot by the camera 36 may be helpful in, for example, medical treatment of the user of the IP device 20, in law enforcement (e.g., when the user activates the panic button 24 in response to a burglary attempt or in response to a threat to the user's physical safety), etc.

Figure 6:
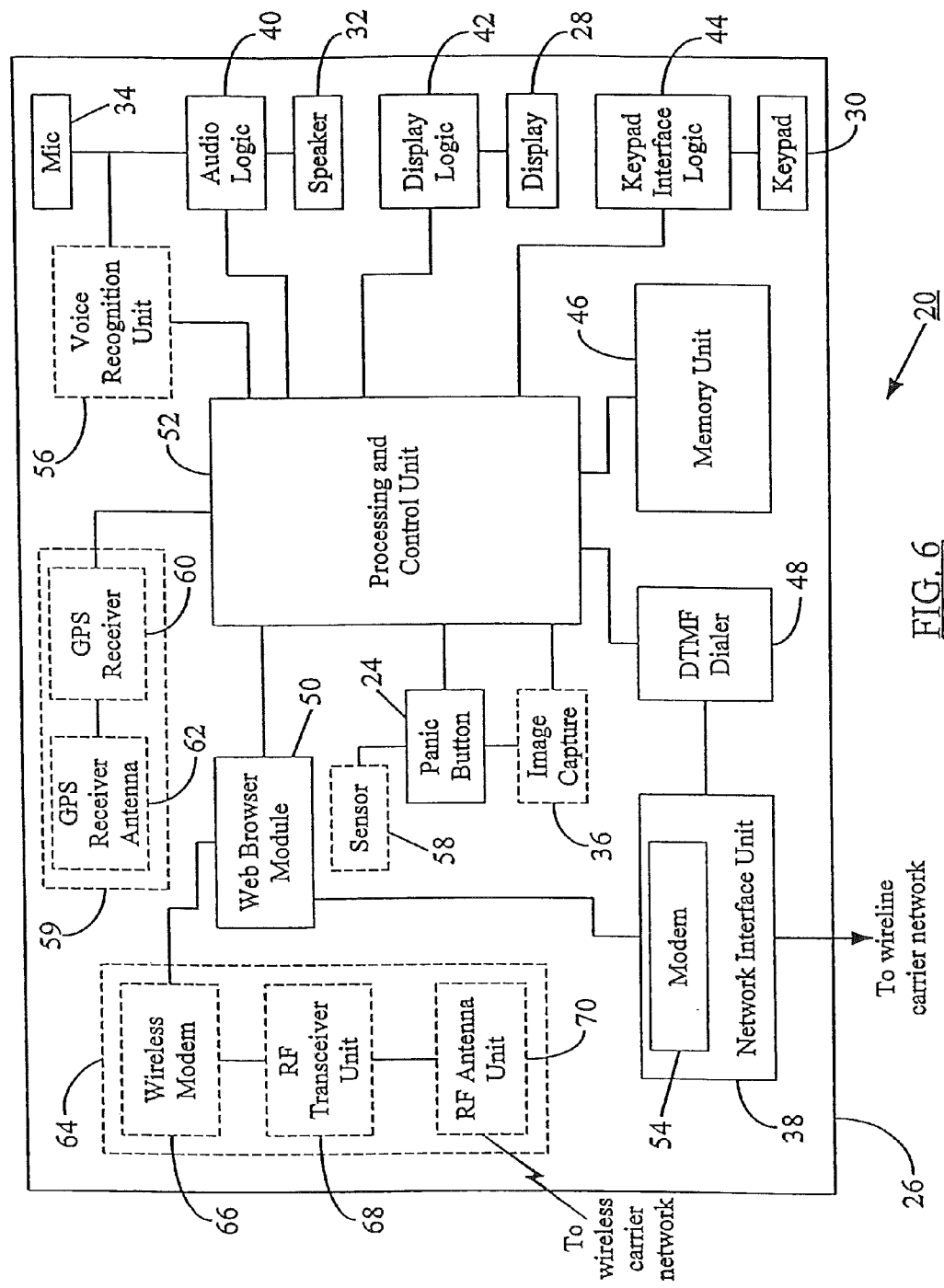
FIG. 6 depicts an exemplary block diagram of constituent circuit blocks in an embodiment of the IP device of the present invention.

The images captured by the digital camera 36 may be transmitted as TCP/IP data packets to the ESC 12 upon activation of the panic button 24. These images may also remain stored in a memory provided within the housing 26 so as to enable security or health personnel to retrieve the images at a later time, for example, by "downloading" the digital image files onto a computer. The images captured by the digital camera 36 may be stored and transmitted as digital data files having a predefined file format including, for example, the GIF (Graphics Interchange Format) format, the TIFF (Tag Image File Format) format, the JPEG (Joint Photographic Experts Group) format, the MPEG (Motion Picture Experts Group) format, or any other desirable format. Except for the addition of the digital camera 36, the IP device 20 in FIG. 5 is identical to that in FIG. 4. FIG. 6 depicts an exemplary block diagram of constituent circuit blocks in an embodiment of the IP device 20 of the present invention. The circuit elements that may be placed within the housing 26 include a network interface unit (NIU) 38, an audio logic unit 40, a display logic unit 42, a keypad interface logic unit 44, a memory or storage unit 46, a DTMF (Dual Tone Multi Frequency) dialer 48 and a web browser module 50. These circuit elements are shown coupled to a processing and control unit (PCU) 52 that manages and controls various operations performed by these circuit elements. The NIU 38 may include a modem 54 so as to enable the web browser module 50 to transmit and receive digital information over a telephone or an ISDN line and to thereby access the Internet. It is noted that all of the circuit elements shown in FIG. 6 need not be included in one housing (e.g., the housing 26). In other words, one or more of the circuit elements shown in FIG. 6 may remain outside of the housing 26. For example, in one embodiment, the display logic unit 42 and the display 28 may not be part of the housing 26. In that embodiment, the housing 26 may be electrically connected (e.g., via a corded, or a cordless or wireless connection) with a remotely located display logic unit 42 and its corresponding display 28.

The network interface unit 38 provides an electrical interface for signals traveling between various circuit elements inside the housing 22 and a wireline carrier network, e.g., the carrier network 14 in FIG. 3, connected to the IP device 20 either directly or via a base unit (not shown) associated with the IP device 20 as discussed hereinbefore. Different signals, such as a dial tone received over a telephone line in the carrier network 14, digits dialed by the DTMF dialer 48, data communication signals (including the TCP/IP emergency request messages) transmitted and/or received by the web browser module 50, etc., may pass through the NIU 38 prior to reaching their appropriate destinations. The NIU 38 may provide signal amplification, for example, in a noisy signal environment. The NIU 38 may also include circuitry for the modem 54 to facilitate data communication for the web browser module 50 over, for example, a telephone line or an ISDN line.

The audio logic unit 40 may be connected to the microphone 34 and the speaker 32. The speaker 32 may be activated by the audio logic unit 40 when the PCU 52 informs the audio logic unit 40 that the panic button 24 has been pushed. Voice messages sent by, for example, the service personnel at the ESC 12, may first be received by the PCU 52 (via the NIU 38) and the PCU 52 may transmit these signals to the audio logic unit 40 to be sent to the speaker 32 for generating audible sound. Alternatively, any digital audio files received by the IP device 20 (using the NIU 38) over the Internet 22 may first be sent to the web browser module 50 to retrieve the audio file data therefrom. The browser module 50 may then send the audio data to the PCU 52, which, in turn, forwards the audio data to the audio logic unit 40 and eventually to the speaker 32. The ESC 12 may be configured to automatically transmit pre-recorded audio information over the Internet 22 (via TCP/IP message packets) when the ESC 12 receives an emergency request message from the IP device 20.

The user of the IP device 20 may speak into the microphone 34 to transmit the user's voice over the Internet 22. The audio logic unit 40 receives the electrical audio signals from the microphone 34 and sends them to the PCU 52, which, in conjunction with the browser module 50, transmits the user's voice over the Internet 22 using the NIU 38. In one embodiment, the user may store the user's personal identification information as a digital audio file in the memory unit 46 by speaking into the microphone 34. The PCU 52 may convert the audio electrical signals received from the audio logic unit 40 into the predetermined digital audio file format and store the user's personal information in the memory unit 46. The personal information may include the user's name, address, any known medical condition, contact information in case of emergency, etc. The digital audio file formats for the user's personal information may include file extensions such as, for example, ".WAV" (wave file), ".AIFF" (Audio Interchange File Format), ".AU" (audio file), etc. Upon activation of the panic button 24, the PCU 52 may retrieve the personal information from the memory 46 and may transmit it to the web browser module 50, which, in turn, may immediately send the information to the ESC 12 via TCP/IP packets sent over the Internet 22.

The display logic unit 42 monitors and manages display functionality for the IP device 20. The PCU 52 may generate proper commands and signals for the display logic unit 42, which, in turn, may control the display of visual information on the display screen 28. The display screen 28 may display various information such as, for example, an e-mail message received from the ESC 12 or any data entered via the keypad 30 or an intimation of which action is being performed by the IP device 20. For example, the browser module 50 may instruct the DTMF dialer 48 (via the PCU 52) to start dialing the telephone number for Internet access. Once the DTMF dialer 48 starts dialing that access number, the PCU 52 may instruct the display logic unit 42 to display a phrase such as "DIALING IN PROGRESS" on the visual display screen 28. Similarly, a message such as "ACCESSING THE INTERNET" may also be sent to the display logic unit 42 (to be displayed on the display screen 28) by the PCU 52 once the PCU 52 receives an indication from the web browser module 50 that Internet access is in progress. Other messages may also be conveniently displayed on the screen 28. For example, as soon as the user presses a key on the keypad 30, the corresponding digit, symbol or command may be displayed on the display screen 28 by the display logic 42.

The keypad interface logic 44 is coupled to the keyboard 30 and receives signals sent from the keyboard 30 when the user presses one or more keys thereon. The user may "program" the IP device 20 with pertinent data about the ESC 12 including, for example, the name of the ESC 12, the IP address of the ESC 12, the telephone number and name of the contact person at the ESC 12, the e-mail address of the ESC 12, etc. These data may be entered using various keys on the keypad 30. The web browser module 50 may need a portion of such data to determine how to access the ESC 12 over the Internet 22. Furthermore, the user may also prefer to enter personal information about the user, e.g., the user's name, the address of the user's contact location, any known medical condition, name and contact information about the user's family physician, etc.

The keypad interface 44 transmits the signals received from the keyboard 30 to the PCU 52 for further processing. The PCU 52 decodes the received signals and accordingly instructs the appropriate circuit elements for necessary action. For example, when the user enters the user's personal information and the data pertaining to the ESC 12, the keypad interface logic 44 may send all the data to the PCU 52, which may instruct the memory unit 46 to store the received data therein. The PCU 52 may store the user's identification information, the ESC 12 access data, etc., in the memory 46 using one of a number of digital text formats, e.g., HTML (Hyper Text Markup Language) format, ASCII (American Standard Code for Information Interchange) format, XML (Extensible Markup Language) text file format developed by W3C (World Wide Web Consortium), etc.

In one embodiment, the housing 26 may include a text-to-speech (TTS) converter (not shown). The TTS conversion functionality may be implemented with appropriate software residing in the PCU 52. The TTS converter may work with an SGML (Standard Generalized Markup Language) format-based TTS markup language. The SGML format may be based on the ASCII text format. An example of an SGML-based TTS markup language includes the STML (Spoken Text Markup Language) developed by Lucent Technologies of Murray Hill, N.J., USA. In that embodiment, the ESC 12 may be configured to transmit to the IP device 20 an e-mail or other response message over the Internet 22 using the SGML format. Such a response message may be generated when the ESC 12 receives the emergency request message from the IP device 20. The response e-mail from the ESC 12 may state in general terms that the ESC 12 has received the help request message and the requested help is being dispatched. This scheme allows for a quick "confirmation" of receipt of the help request message from the IP device 20 and also for an expedited "response" back to the IP device 20 to pacify and comfort the user of the IP device 20 prior to the arrival of emergency personnel. The TTS converter may convert the text file received from the ESC 12 into an STML file that can be audibly played back by the audio logic unit 40. The user of the IP device 20 can thus hear, in a synthesized voice, the content of the message sent by the ESC 12 in a digital text format.

The memory or storage unit 46 provides memory for storage of data, such as the user's personal information as discussed hereinbefore. The data stored locally in the memory unit 46 may be text, audio or video data and may include a number of digital file formats as described hereinbefore. For example, data that may be sent over the Internet 22 may be in the HTML or the WML (Wireless Markup Language) formats depending on whether the web browser module 50 is used with a wireline carrier network or a wireless carrier network respectively as described hereinbelow. The memory unit 46 may be located inside the housing 26 or, alternatively, may be supplied as a memory cartridge (not shown) that may be attached to the housing 26 at an appropriate adapter slot (not shown) provided on the housing 26.

The memory unit 46 may include volatile and/or non-volatile memory, such as RAM (Random Access Memory), ROM (Read Only Memory), EEPROM (Electrically Erasable Programmable Read Only Memory), flash memory or other similar memory units. A volatile memory may lose the data stored therein if the power applied thereto is removed. The personal information about the user (as an audio file or as a text file) as well as the contact information about the ESC 12 may be stored in the non-volatile portion of the memory 46. On the other hand, a paging message may be stored in the volatile portion (or temporary storage) of the memory 46 for an IP device 20 that may also function as a wireless pager.

In one embodiment, the DTMF (Dual Tone Multi Frequency) dialer 48 communicates with the PCU 52 and receives the telephone number sent to the PCU 52 by the web browser module 50 for dial-in Internet access. The telephone number may be for direct access to the ESC 12 or it may be for an ISP (Internet Service Provide) through which the emergency request message may be sent to the ESC 12 over the Internet 22. The DTMF dialer 48, in turn, generates corresponding DTMF signals to be sent to the local telephone switching office in the carrier network 14 via the NIU 38. The DTMF signals may be sent over a telephone line either directly from the IP device 20 or from a corresponding base unit (not shown) for the IP device 20 as discussed hereinbefore.

The web browser module 50 may include software code or routines which, when executed by the PCU 52, perform web browser functions upon execution. In one embodiment, the web browser module 50 may be implemented using a combination of software and hardware elements. The web browser software may include, for example, an HTML browser or a WAP (Wireless Application Protocol) browser because of the small size and portable nature of the IP device 20 and because of the smaller display 28 and limited memory space (in the memory unit 46) available for the IP device 20. A commercially available HTML browser, for example, the Netscape Navigator™ or the Microsoft Internet Explorer™ may be selected for the web browser module 50. In case of a WAP browser, a commercially available WAP-compliant microbrowser (or wireless web browser) used, for example, in Nokia™ 7100 series cell phone or in the Palm Pilot™ hand-held computer versions 5.0 or 6.0 may be selected. The HTML browser may "read" information received or stored in the HTML format, whereas the WAP browser may be able to "read" information having WAP content (e.g., information in the WML (Wireless Mark-up Language) format). The web browser software, upon execution, may access a physical communication medium (e.g., a telephone line) in the carrier network 14 using the modem 54 and may dial into an ISP (Internet Service Provider) server (not shown). The ISP server thus allows the web browser module 50 to connect to the Internet 22.

The web browser 50 may be activated using one or more keys on the keypad 30 and may be used for surfing the world wide web portion of the Internet. Furthermore, the web browser module 50 may also be automatically activated once the panic button 24 is pressed by the user of the IP device 20. In that case, the web browser 50 may retrieve (via the PCU 52) relevant locally-stored information (e.g., the web address of the ESC 12 or the personal information about the user) from the memory unit 46 and transmit an appropriate portion of that information over the Internet 22 in response to the activation of the panic button 24. The web browser module 50 interacts with the PCU 52 to execute necessary software routines for Internet access. The software routines, upon execution, activate the modem 54 in the NIU 38 to establish an electrical connection with a wireline carrier network (e.g., via a telephone line (not shown)) to accomplish dialed Internet access. In one embodiment, the web browser module 50 (including its hardware and/or software elements) may be a part of the PCU 52 and the PCU 52 may directly perform web browsing or information delivery over the Internet 22.

Inclusion of the web browser 50 within the IP device 20 results in a standardized information interface for the IP device 20 because it dispenses with the need to have a proprietary format for information transmission, storage and display. The emergency help request messages does not have to be in a proprietary format for the ESC 12 to be able to read them, but, instead, the messages to and from the ESC 12 may be in a generally available text format, e.g., the HTML format or the WML format. This allows for ease of communication between the user and the ESC 12 using TCP/IP data packets over the Internet 22.

The PCU 52 manages and controls various operations performed by different circuit elements connected thereto. The PCU 52 functions as a centralized location to send and receive various commands and information. For example, the PCU 52 may receive a signal from the panic button 24 when the user activates the panic button 24. In response, the PCU 52 may execute the web browser software in the browser module 50 to initiate an Internet connection. The PCU 52 may receive a responsive message, e.g., in an e-mail format, from the ESC 12 (via the browser module 50) and may, in turn, instruct the display logic 42 to display the message on the display screen 28. Alternatively, the PCU 52 may instruct the TTS converter (not shown) to audibly "play" the message text using the audio logic unit 40 and the speaker 32 as described hereinbefore. During web browsing, the PCU 52 may also execute audio and video data files received from the Internet 22 using the web browser module 50 and send appropriate audio and video signals to the audio logic unit 40 and the display logic unit 42 respectively.

In one embodiment, the PCU 52 may time-stamp each outgoing TCP/IP message in response to the activation of the panic button 24. Thus, the time when the emergency arose may be accurately traced by looking at the received emergency help request message at the ESC 12 (or at the SSP 18 in FIG. 8). This may be of help to the ESC 12 in organizing its emergency help efforts. Some exemplary PCUs include the Intel x86 series microprocessors or the Motorola 68x series microprocessors.

The modem 54 may be used to transmit and receive digital data over a wireline carrier network 14, e.g., the PSTN or the ISDN. The modem 54 modulates and demodulates the digital information transmitted and received respectively over a physical communication medium, e.g., a PSTN telephone line or an ISDN line. The modem 54 may employ one or more of a number of modulation schemes including, for example, FSK (frequency shift keying), DPSK (differential phase shift keying), QAM (quadrature amplitude modulation) and TCM (trellis-coded modulation). The modem 54 may function in a full duplex communication mode allowing simultaneous transmission and reception of electrical signals. The modem 54 may perform error correction for transmitted and received data. The data communication speed of the modem 54 may be, for example, 56 kbps (kilo bits per second) with automatic fall-back capability in the event of noisy line conditions or due to a mismatch between the data communication speeds of the modem 54 and the device with which the modem 54 is communicating. Any Hayes® compatible modem may be used for the modem 54.

The IP device 20 may include a number of optional circuit elements within the housing 26 as indicated by dotted boxes in FIG. 6. One optional circuit element is the digital camera or image capture device 36 discussed hereinbefore with reference to FIG. 5. The image capture device 36 is shown connected to the panic button 24 to allow for instant activation of the image capture device 36 in response to the activation of the panic button 24. Some additional optional circuit elements may include a voice recognition unit 56; a sensing device or a sensor 58; a user location identifier 59 including a GPS (Global Positioning System) receiver 60 and a GPS receiver antenna 62; and a wireless data communication module 64 including a wireless modem 66, an RF (Radio Frequency) transceiver unit 68 and an RF antenna unit 70.

The voice recognition unit (VRU) 56 is connected to the microphone 34 to receive speech and other audio signals captured by the microphone 34. The voice recognition functionality may be implemented with hardware and/or software components in the VRU 56. The VRU 56 may be programmed to identify and recognize the voice of the user of the IP device 20. Furthermore, the VRU 56 may be configured to recognize specific frequencies in the user's voice and, upon such recognition, may convey appropriate message to the PCU 52 informing the PCU 52 to activate the web browser module 50 and to transmit an emergency help request message to the ESC 12 over the Internet 22. For example, the VRU 56 may recognize only a shrill or a high-pitched voice pattern generated when the user of the IP device 20 senses danger (e.g., a burglary attempt or an actual or impending physical assault on the user) or is in need of emergency help. Such an arrangement may be necessary to avoid false transmission of emergency help request messages (or "false alarms") to the ESC 12. For example, if the VRU 56 is mistakenly configured to activate the emergency help request feature (via the PCU 52) whenever the VRU 56 recognizes the user's voice (e.g., when the user performs normal conversation), this may cause undesirable transmissions of help request messages to the ESC 12. This may be subversive to the purpose of the emergency help request feature and may damage the credibility of the user as a person in need of emergency help.

In one embodiment, the VRU 56 may also have speech recognition capability to identify the words spoken by the user in distress. The VRU 56 may then send those recognized words as a digital text file to the PCU 52, which, in turn, may transmit the digital text file along with any other emergency help request message text to the ESC 12. This may inform the ESC 12 of what was spoken by the user immediately prior to requesting emergency help and may also allow the ESC 12 to commence appropriate relief efforts in response. For example, in addition to dispatching medical workers, the ESC 12 may also dispatch fire fighters if the user's spoken words indicate that the user is caught in a fire.

The sensor or the sensing device 58 may sense a physical condition afflicting the user of the IP device 20. For example, if the user is a heart patient, the sensor 58 may continuously monitor the user's heartbeats to identify any abnormality therein. Upon detecting an abnormal condition, the sensor 58 may trigger the panic button 24, which, in turn, may inform the PCU 52 to transmit (using the web browser module 50) an emergency relief request message to the ESC 12. In an alternative embodiment, the output of the sensor 58 may be connected directly to the PCU 52 instead of through the panic button 24. The sensor 58 may be configured to sense other emergency conditions as well. For example, the sensor 58 may sense abnormal blood pressure levels or unusual body temperature. In one embodiment, the sensor 58 may contain circuitry to detect specific frequencies contained in the sound of a breaking glass to immediately inform the ESC 12 (via automatic activation of the panic button 24) of any burglary attempt at the user's household. The user location identifier 59 within the housing 26 is shown to include a GPS receiver 60 and a GPS receiver antenna 62. The GPS receiver antenna 62 may be provided on the housing 26 to continuously receive location signals from geostationary satellites and transfer those signals to the GPS receiver 60 to identify the current location of the IP device 20 and, hence, of the user carrying the IP device 20. Instead of a built-in location identifier 59, the housing 26 may be provided with a port (not shown) to receive an external location identifier (with or without the receiver antenna 62) that may be attached to the port when needed. The GPS location identifier 59 may perform better in an outdoor environment. This may be useful when the user is on the road or at a remote location where access to a telephone may not be easily available. In that case, the user's location may be transmitted along with the emergency help request message to the ESC 12. The user location identifier 59 may supply the PCU 52 with the requisite location information and the PCU 52, with the help of an appropriate web browser module 50 and the wireless data communication module 64 (described hereinbelow), may send the emergency help request message along with the user location information over the Internet 22 to the ESC 12. The commercially available Megellan GPS receiver may be included as part of the user location identifier 59.

The wireless data communication module 64 employs wireless devices to transfer data and information between the IP device 20 and the ESC 12 over the Internet 22. An antenna, e.g., an RF (radio frequency) antenna 70, may be provided on the housing 26 of the butt set 74 to allow wireless data communication. In the event of wireless data communication, the NIU 38 (including the wireline data modem, i.e., the modem 54) may remain inactive. Furthermore, when the IP device 20 is equipped with cellular telephone features or paging device features, the housing 26 for that IP device 20 may include only the wireless data communication module 64 and may omit the NIU 38. Here, data communication may be accomplished via a wireless modem 66 using a wireless carrier network 14. If the wireless carrier network 14 is a cellular network (e.g., a TDMA-based wireless network, a CDMA-based (Code Division Multiple Access) wireless network, or a GSM-based (Global System for Mobile Communications) wireless network), then the wireless modem 66 may be capable of data transfer using the message format supported by the given cellular network.

The web browser module 50 in the housing 26 may be configured to transfer data over a wireless carrier network 14 and, hence, the web browser module 50 may be connected to the wireless modem 66. The web browser module 50 may include a WAP (Wireless Application Protocol) browser to access the Internet 22. The WAP browser in the web browser module 50 may transfer data over the Internet 22 using a WAP-supported data format, e.g., the WML (Wireless Markup Language) format. In one embodiment, the web browser module 50 may be configured to responsively connect to a wireline data modem (e.g., the modem 54) or a wireless modem 66 depending on the desired mode of data communication. A web browser module 50 with an HTML browser may be similarly configured to perform data transmission and reception operations using wireless devices (similar to, for example, the wireless data communication module 64). The IP device 20 may also include a web browser module 50 with browser software that supports a content format that is different from HTML or WML such as, for example, the JavaScript scripting language. An IP device may be conveniently designed to include such a web browser module for data communication.

The RF transceiver unit 68 sends RF signals to the RF antenna 70 for transmission to the wireless carrier network 14 and receives RF signals from the RF antenna 70 and forwards them to the wireless modem 66 for further processing. The RF antenna 70 provides the necessary signaling interface between a wireless carrier network 14 and the web browser module 50 that needs to access the wireless network 14.

The wireless carrier network 14 may be, for example, an analog wireless network (e.g., the AMPS (Advanced Mobile Phone System) network), a digital wireless network including cellular networks (e.g., the TDMA or CDMA-based wireless networks), a wireless LAN (Local Area Network) or a WLL (Wireless Local Loop) configuration. A portion of the wireless carrier network 14 may include one or more microwave links for satellite-based communication. A WAP proxy/server (not shown) may be included as part of the wireless carrier network 14 to facilitate access to the Internet 22 using a wireless IP device 20 (e.g., a cellular telephone equipped with the panic button 24).

The wireless modem 66 may perform necessary data encoding for the data received from the WAP browser in the web browser module 50 to prepare the data (e.g., an emergency help request message) to be sent to the wireless carrier network 14 and eventually to the ESC 12 over the Internet 22. A corresponding decoding may be performed by the wireless modem 66 upon receipt of data (e.g., a confirmation message from the ESC 12) from the RF transceiver unit 68 prior to sending the decoded data to the WAP browser (in the web browser module 50) for further processing. The Ricochet SE wireless modem manufactured by Metricom, Inc. of Los Gatos, Calif., USA or a wireless modem manufactured by US Robotics may be selected for the wireless modem 66.

The RF transceiver unit 68 modulates data received from the wireless modem 66 to be transmitted over an RF transmission channel linking the housing 26 with the wireless carrier network 14. This modulated data is then wirelessly transmitted to the carrier network 14 (and, hence, to the Internet 22) by the RF antenna unit 70. Upon reception of data or information from the wireless carrier network 14 (e.g., an Internet e-mail message received from the ESC 12 over the Internet 22), the RF antenna unit 70 forwards the RF-modulated data to the RF transceiver unit 68, which demodulates the data and sends it to the wireless modem 66 for further processing and transfer to the WAP browser in the web browser module 50.

Figure 7:
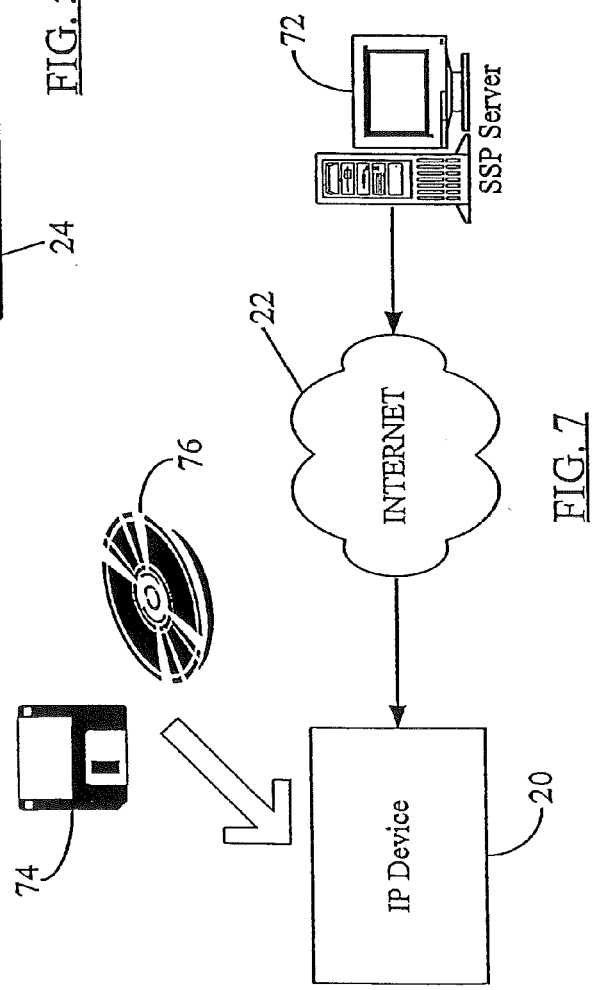
FIG. 7 shows two ways of downloading emergency reporting software in an embodiment of the IP device according to the present invention and implementing the panic button functionality through software.

FIG. 7 shows two ways of downloading emergency reporting software in an embodiment of the IP device 20 according to the present invention and implementing the panic button functionality through software. In one embodiment, the support service provider (SSP) 18 (FIGS. 2, 8 and 9) may operate a computer server 72 or any other remote data supplying device that may download the requisite emergency reporting software onto the IP device 20 via a communication network (here, the Internet 22). In other words, the IP device 20 may first access the SSP server 72 via the Internet 22 and thereafter activate the software download process. In alternative arrangements, the communication network linking the IP device 20 and the SSP server 72 may include (in addition to or in place of the Internet 22) a local area network (LAN), a wide area network (WAN), a wireless communication network (e.g., the cellular telephone network), or a combination of one or more of these networks. The support service provider 18 is an entity (commercial or non-commercial) that may operate independently of the ESC 12. The SSP 18 may distribute the IP device 20 and may provide special access to the SSP server 72 or other SSP-supported services for SSP's subscribers. Additional discussion about SSP 18 is given hereinbelow with reference to FIGS. 8 and 9.

In another embodiment, the IP device 20 may be provided with one or more built-in hardware storage drives, e.g., a floppy disk drive or a compact disc drive (not shown). Alternatively, the housing 26 may include a communication port (e.g., a serial communication port) (not shown) to which an external storage drive may be attached to transfer data into the memory 46 within the housing 26. A floppy disk 74 or a compact disc 76 or any other storage medium (e.g., magnetic or optical) containing the requisite emergency reporting software may be provided by the SSP 18 to the user/purchaser of the IP device 20 to be inserted into the corresponding storage drive to download the software into the memory 46.

The emergency reporting software (ERS) is application software that may simulate the functionality of the hardware panic button 24 in software. Thus, the hardware circuitry associated with the panic button 24 may be eliminated. Instead, the emergency reporting software may get executed (by the PCU 52) whenever the user pressed the panic button 24 on the face of the housing 26. The execution of the ERS may result in activation of the web browser module 50 to perform necessary data transmission (e.g., transmission of the emergency help request message to the ESC 12) over the Internet 22. In an alternative embodiment, a hardware panic button 24 may not be provided on the face of the housing 26. Instead, the display screen 28 may be made touch-sensitive and the ERS may permanently display an icon (not shown) on the display screen 28 identifying the panic button 28. The user may simply touch the icon on the display screen 28 and, in response, the PCU 52 may execute the ERS to send the emergency help request message to the ESC 12 over the Internet 22.

Figure 8:
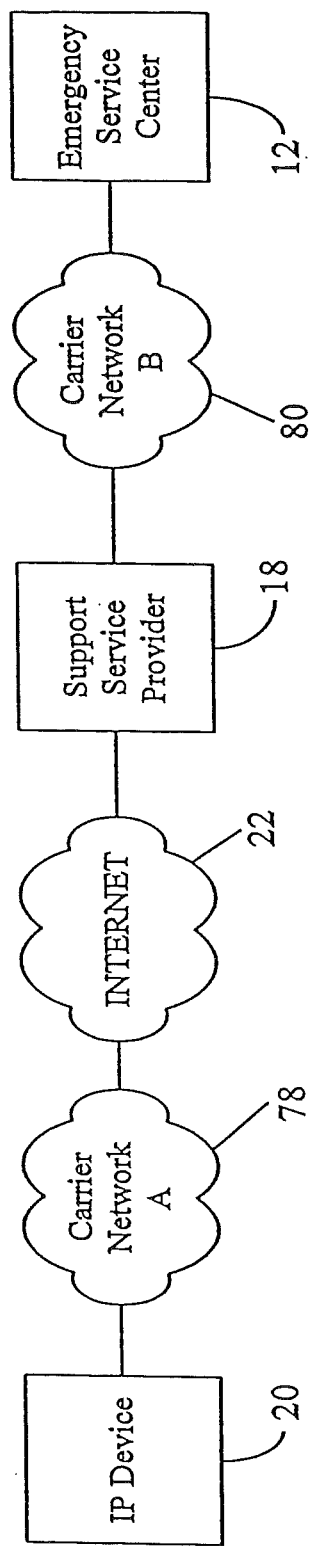
FIG. 8 illustrates an arrangement showing how a support service provider forwards an emergency help request message from the IP device to the emergency service center.

FIG. 8 illustrates an arrangement showing how the support service provider (SSP) 18 forwards an emergency help request message from the IP device 20 to the emergency service center 12. The SSP 18 acts as an intermediary that first receives the emergency requesting message from the IP device 20 over the Internet 22. Thereafter, the SSP 18 may forward that message to the ESC 12 or may itself contact the ESC 12 on behalf of the user of the IP device 20. The SSP 18 may also explain the potential problem to ESC 12 personnel based on any information contained in the message received from the IP device 20 or based on any earlier-stored information about the user when the user first subscribed to the SSP's service.

As noted before, the SSP 18 may provide subscription-based emergency assistance service or, alternatively, the SSP 18 may be a not-for-profit organization offering help to a class of citizens, e.g., the elderly. The SSP 18 may sell, rent or offer for free the IP devices 20 to its subscribers. The SSP 18 may also maintain a database of all of its subscribers with relevant information about them, e.g., known medical conditions, an emergency contact address, a home address, etc. The SSP 18 may thus act as a link between the user of the IP device 20 and the service personnel at the ESC 12 who may need certain information about the user prior to recommending appropriate emergency relief.

The connection between the IP device 20 and the SSP 18 via a carrier network A 78 and the Internet 22 is similar to the arrangement described hereinbefore with reference to FIG. 3. In FIG. 8, the carrier network A 78 may be identical to the carrier network 14 (FIG. 3) and the recipient of the message, i.e., the SSP 18 may be analogized with the ESC 12 in FIG. 3. Therefore, in view of the discussion given hereinbefore, additional discussion of message delivery operation from the IP device 20 to the SSP 18 is not provided herein.

The SSP 18 is shown connected to the ESC 12 via a carrier network B 80. The carrier network B 80 may be a part of the carrier network A 78. For example, both the carrier network A 78 and carrier network B 80 may be public switched telephone networks. However, the telephone number dialed by the IP device 20 to deliver an emergency message to the SSP 18 via the carrier network A 78 (and also via the Internet 22) may be different from the telephone number dialed by the SSP 18 to inform the ESC 12 (via carrier network B 80) of the user's emergency need. It is noted that the discussion given hereinbefore with respect to carrier network 14 applies equally to one or both of the carrier network A 78 and carrier network B 80. For example, carrier network B 80 may be a wireless carrier network (e.g., a cellular phone network) whereas the carrier network A 78 may be a wireline carrier network (e.g., the PSTN).

In one embodiment, the carrier network B 80 may also include the Internet 22. In other words, the SSP 18 may first receive the emergency help request message from the IP device 20 and may, in turn, forward that message (with or without additional information) to the ESC 12 over the Internet 22 (i.e., via the carrier network B 80). This may be helpful to prevent confusion and flooding of TCP/IP messages at the ESC 12 when different users directly contact the ESC 12. Instead, the SSP 18 may function like a "hub" that receives messages from all of its subscribers and then forwards them to the ESC 12. The ESC 12 may thus deal with only one entity, i.e., the SSP 18. Further, the ESC 12 may provide the SSP 18 with a special access code or identification number to indicate (to the personnel at ESC 12) that the messages are from the subscribers of the SSP 18. The ESC 12 may then, if needed, inquire further with the SSP 18 (regarding the nature or severity of the emergency condition) prior to dispatching emergency help.

Figure 9:
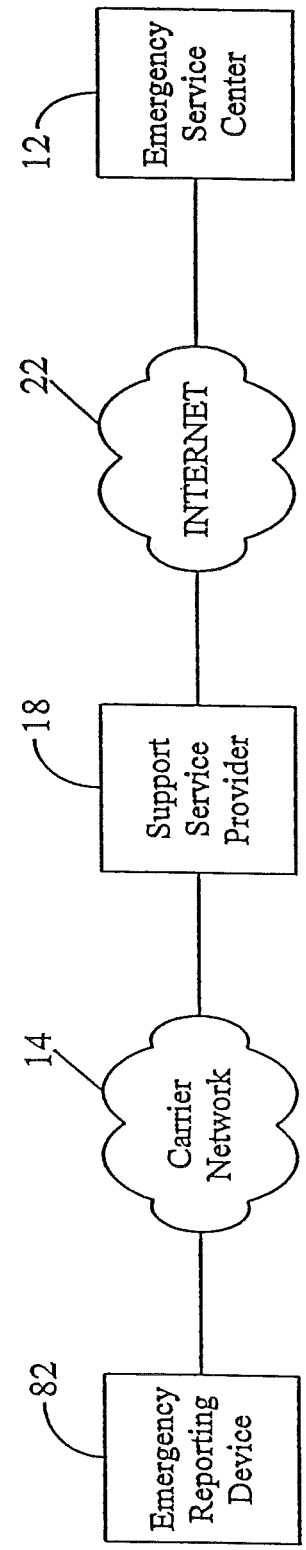
FIG. 9 depicts an alternative arrangement whereby the support service provider delivers the emergency help request message received from an emergency reporting device to the emergency service center over the Internet.

FIG. 9 depicts an alternative arrangement whereby the support service provider 18 delivers the emergency help request message received from an emergency reporting device (ERD) 82 to the emergency service center 12 over the Internet 22. Here, the SSP 18 first receives the emergency help request message via the carrier network 14 that does not include the Internet 22. In other words, the emergency help request from the ERD 82 may not be in the form of a TCP/IP message. Instead, the SSP 18 may "convert" the receive non-TCP/IP message into a TCP/IP message to be sent to the ESC 12 over the Internet 22. The SSP 18 may optionally time-stamp the TCP/IP message prior to sending the message to the ESC 12 to indicate the time the emergency was reported. The time-stamping by the SSP 18 may be based on the time-stamp, if provided, in the original message received from the ERD 82.

In the method of message delivery illustrated in FIG. 9, the ERD 82 may include an IP device or a non-IP device, with or without a built-in panic button (in hardware or software implementations). In other words, the ERD 82 may include, for example, a regular desktop telephone or a cellular telephone (not shown). Even the IP device 20 may qualify as an ERD 82 when, for example, the IP device 20 sends a non-TCP/IP emergency help request message (e.g., a regular voice message over a telephone call) to the SSP 18. The user of the ERD 82 may explain the emergency situation to an operator at the SSP 18 or, alternatively, the user of the ERD 82 may simply press a panic button provided on the ERD 82 to identify the user as the person in need of emergency help. In the latter situation, the SSP 18 may obtain more information about the user by simply consulting its subscriber database that may contain the user's personal, medical and contact information as discussed hereinbefore.

Once the SSP 18 receives a live message or an indication (e.g., when a panic button is pushed) from the user of the ERD 82 that the user needs emergency help, the SSP 18 (i.e., an operator at the SSP 18) may send an emergency help request message to the ESC 12 over the Internet 22. The message from the SSP 18 may be pre-formatted and may also include text (obtained from searching the subscriber-database maintained by the SSP 18) containing additional personal information about the user to assist ESC 12 personnel in providing emergency help to the user.

In the arrangements of FIGS. 8 and 9, the SSP 18, as part of the emergency help request message to the ESC 12, may include information about the identity of the user (e.g., the name of the user or other physical mark or identification of the user), the location of the user (i.e., the address of record with the SSP 18 or the address where the emergency service is to be sent), medical information about the user (e.g., prior known medical conditions or allergies), the time when the user requested help and an indication of a probable cause of the user's distress (e.g., illness, injury, fire, etc.) in the message. As noted hereinbefore, part or all of such user-specific information may be already present in the emergency message received from the IP device 20. In one embodiment, the SSP 18 may add any missing and relevant user-specific information prior to sending the emergency requesting message to the ESC 12. The carrier network 14, as described hereinbefore, may be a wireline network or a wireless network or a combination of both. Thus, the message received at the SSP 18 may not be in the TCP/IP format. However, the SSP 18 may "convert" the received message into a TCP/IP message to facilitate its transmission over the Internet 22. The SSP 18 may charge a nominal amount (e.g., one dollar) per emergency help request from a user. Alternatively, the SSP 18 may charge a flat sum of money as subscription fees for a user to avail of SSP's emergency assistant services.

An advantage of the message transfer arrangements illustrated in FIGS. 8 and 9 is that the user or operator of the ERD 82 (which may include the IP device 20 as mentioned hereinbefore) need not worry about the identity or contact information about the ESC 12. The SSP 18 coordinates the emergency help on behalf of the user—i.e., the subscriber of the SSP's services. Furthermore, transmission of packetized data (e.g., through TCP/IP messages) over the Internet 22 allows for flexibility in data transmission. For example, the user and/or the SSP 18 may transmit a TCP/IP emergency request message or Internet e-mail with an indication or message flag set to indicate, to the corresponding carrier network 14, 78 or 80 and/or the Internet 22, that the transmitted message be given a designated priority (e.g., highest priority) over other pending data packets to be sent over the carrier network and/or the Internet 22. Such a "marking" of messages may be permitted when the carrier network 14, 78 or 80 or the Internet 22 implements a class-based service scheme as discussed hereinbefore.

An additional advantage of the Internet-based emergency message delivery methods of FIGS. 8 and 9 is that the user need not wait for a free line to speak with an operator at the ESC 12. The user may simply press the panic button 24 (FIG. 4) to automatically send the emergency help request message or to call the SSP 18 over a dedicated contact number provided by the SSP 18. Message delivery to the ESC 12 over the Internet 22 relieves the user of waiting to speak with an operator at the ESC 12 or to reach an operator initially. Furthermore, in one embodiment, the user may transmit audible messages without actually reciting the message in the user's voice. Here, the IP device 20 (in the arrangement of FIG. 8) or a similar circuit arrangement at the SSP 18 (in the arrangement of FIG. 9) may convert the textual message (e.g., the user's personal, medical and contact information) to be transmitted to the ESC 12 into an audio file containing a synthesized voice message corresponding to that textual message prior to sending the audio file to the ESC 12 over the Internet 22. An operator at the ESC 12 may thus "listen" to the text file upon receipt of the emergency message.

The foregoing describes exemplary embodiments of an IP device having a built-in panic button that may be implemented in hardware or software. Activation of the panic button by a user in need of emergency help results in automatic transmission of one or more TCP/IP messages over the Internet to an emergency service center requesting emergency help and identifying the user in need of such help. The emergency service center may also communicate, e.g., via Internet e-mail, with the IP device (and, hence, with the user) prior to dispatching emergency help. A support service provider may commercially provide Internet-based emergency message delivery services to its subscribers. This may be useful in many situations, for example, when the person in need of help is speech-impaired, disabled or in a situation that prevents that person from orally requesting emergency help. The resources of the Internet may thus be advantageously harnessed to provide emergency help.

While several embodiments of the invention have been described, it should be apparent, however, that various modifications, alterations and adaptations to those embodiments may occur to persons skilled in the art with the attainment of some or all of the advantages of the present invention. It is therefore intended to cover all such modifications, alterations and adaptations without departing from the scope and spirit of the present invention as defined by the appended claims.

What is claimed is:

1. A device for requesting emergency assistance, comprising:
 a processing unit;
 a browser module to download emergency reporting software over a network, the emergency reporting software for execution by the processing unit;
 a touch-sensitive display screen;
 a display logic unit coupled to the processing unit and the display screen;
 wherein the display screen displays an icon, the display logic unit to send a first indication to the processing unit when a user touches the icon;
 a communication module coupled to the processing unit, the processing unit to send a second indication to the communication module, wherein the second indication is in response to the first indication;
 the communication module to deliver a help request message to an emergency service center, wherein delivering the help request message is in response to the second indication, the help request message being in a format for delivery to a support service provider prior to transmission to the emergency service center;
 wherein the help request message contains an identity of the user, a location of the user, medical information about the user and a time when the user activated the emergency alert activation function.

2. The device of claim 1, wherein the help request message further contains an indication of a probable cause for activation of the emergency alert activation function.

3. The device of claim 1, further comprising a user location identifier coupled to the processing unit, the user location identifier to ascertain a location of the user activating the emergency alert activation function.

4. The device of claim 1, the communication module to deliver the help request message via a wireless telecommunication network including a cellular network.

5. The device of claim 1, further comprising a memory unit coupled to the processing unit, the memory unit to store therein the help request message in Internet protocol format.

6. The device of claim 1, wherein:
 the display logic unit to display text of the help request message on the display screen in a user-understandable format.

7. The device of claim 1, further comprising:
 a microphone; and
 an audio logic unit coupled to the microphone and the processing unit, the audio logic unit to receive speech signals from the microphone and send the speech signals to the processing unit; and
 a voice recognition unit coupled to the microphone and the processing unit, the voice recognition unit to identify an emergency utterance in the speech signals and to send a third indication thereof to the processing unit, and the processing unit to send the second indication to the communication module in response to the third indication.

8. The device of claim 1, further comprising a sensor coupled to the emergency alert activation function, the sensor to sense a physical condition being experienced by the user and to activate the emergency alert activation function in response to the physical condition.

9. The device of claim 8, wherein the physical condition includes an abnormality in blood pressure level and heartbeat.

10. The device of claim 1, further comprising an image capture device coupled to the emergency alert activation function and the processing unit, the image capture device to be activated in response to the first indication, and wherein upon the first indication the image capture device to capture an image of the physical vicinity of the user and to transmit the image to the processing unit, wherein the help request message includes the image acquired with the image capture device.

11. The device of claim 1 wherein the help request message is transmitted using instant messaging functionality.

12. The device of claim 10 wherein the image capture device rotates to capture a plurality of images over circular view angle.

13. The device of claim 12 wherein circular view angle is approximately 360 degrees.

* * * * *